United States Patent [19]

Henkelmann et al.

[11] Patent Number: 4,853,481

[45] Date of Patent: Aug. 1, 1989

[54] PREPARATION OF ALKYL-SUBSTITUTED AROMATIC KETONES

[75] Inventors: Jochem Henkelmann, Mutterstadt; Manfred Eggersdorfer, Frankenthal; Walter Grosch, Edingen-Neckarhausen; Alfred Schuhmacher, Ludwigshafen; Hardo Siegel, Speyer, all of Fed. Rep. of Germany

[73] Assignee: BASF Aktiengesellschaft, Ludwigshafen, Fed. Rep. of Germany

[21] Appl. No.: 126,868

[22] Filed: Nov. 30, 1987

[30] Foreign Application Priority Data

Dec. 6, 1986 [DE] Fed. Rep. of Germany ....... 3641793

[51] Int. Cl.$^4$ ........................................... C07C 51/083
[52] U.S. Cl. .................................. 562/460; 568/319; 562/459
[58] Field of Search ................. 568/319, 323; 562/460

[56] References Cited

U.S. PATENT DOCUMENTS 4,087,458  5/1978  Emori et al. ...................... 560/460

FOREIGN PATENT DOCUMENTS

| 768727 | 11/1971 | Belgium | 560/460 |
| 0178184 | 4/1986 | European Pat. Off. | 568/319 |
| 2720294 | 11/1977 | Fed. Rep. of Germany | 560/460 |
| 61-243043 | 10/1980 | Japan | 560/460 |
| 61-158948 | 7/1986 | Japan | 560/460 |
| 62-93255 | 4/1987 | Japan | 560/460 |
| 62-142139 | 6/1987 | Japan | 560/460 |

OTHER PUBLICATIONS

Ota, Chem. Abst., vol. 106, #66873a (1987).
C. A. Olah, Friedel Crafts and Related Reactions, vol. I, p. 207 (1963), and vol. III, part I, pp. 549, 550, Interscience (1964), (two separate references).

*Primary Examiner*—James H. Reamer
*Attorney, Agent, or Firm*—John H. Shurtleff

[57] ABSTRACT

Alkyl-substituted aromatic ketones are prepared by reacting alkylbenzenes with carboxylic anhydrides in the presence of a Friedel-Crafts catalyst by performing the reaction in the presence of a tertiary amine or diamine.

15 Claims, No Drawings

PREPARATION OF ALKYL-SUBSTITUTED AROMATIC KETONES

The present invention relates to an improved process for preparing an alkyl-substituted aromatic ketone by reacting an alkylaromatic with a carboxylic anhydride in the presence of a Friedel-Crafts catalyst.

The Friedel-Crafts acylation of aromatics, ie. the introduction of an acyl group into aromatic compounds such as alkylbenzene by reacting an acylating agent with an aromatic in the presence of certain metal halides, for example aluminum chloride, is common knowledge; see for example Houben-Weyl, Methoden der org. Chem. vol. VII/2a, 1973, p. 15–39. The disadvantage with this process is the occurrence of side reactions, in particular when alkyl-substituted aromatics are acylated. For instance, resinous byproducts are formed, and the alkyl group becomes detached and undergoes isomerization in particular when aromatics are reacted with secondary or tertiary alkyl radicals. As suggested in various publications, these side reactions are thought to be caused by an interaction of $AlCl_3$ and hydrogen chloride, which, if not present in the catalyst, is formed during the Friedel-Crafts acylation (see C. A. Olah, Friedel-Crafts and Related Reactions, vol. I, p. 207 and vol. III, part I, p. 550 et seq., Interscience 1964). To suppress the isomerization, it is recommended that the hydrohalic acid be removed by applying reduced pressure to the reaction system or by passing dry air or inert gases through it (see Olah, vol. III, p. 549 and references cited therein). These measures are taken up in German Published Application DAS No. 2,720,294. In some instances they remove substantial amounts of reactants from the reaction mixture, not only necessitating expensive subsequent waste gas scrubbing but also leading to poorer yields. In addition, these measures are difficult to put into effect in industry. For instance, it is very difficult to introduce the gas quantity required into the reaction mixture. Complete suppression of alkyl group detachment and isomerization is not possible with these measures, which is why product mixtures are obtained.

The tendency of the alkyl group to isomerize is particularly disadvantageous in the case of the synthesis of alkylbenzoylbenzoic acids from which, by cyclization, it is possible to prepare alkylanthraquinones which are useful for preparing hydrogen peroxide. According to German Laid-Open Application DOS No. 2,013,299, the best yields of hydrogen peroxide per kg of reaction solution are obtained when 2-tert.-amylanthraquinone only is used, and not a 2-sec.-isoamylanthraquinone isomer. Under the above-mentioned conditions, however, the products obtained are always isomeric mixtures containing a high proportion of 4-sec.-isoamylbenzoylbenzoic acid, which on cyclization likewise produces a mixture of 2-tert.-amylanthraquinone and 2-sec.-isoamylanthraquinone.

It is an object of the present invention to provide an improved process for preparing alkyl-substituted aromatic ketones whereby any detachment or isomerization of the alkyl group is suppressed or substantially avoided. More particularly, it should provide access to 4-tert.-amylbenzoylbenzoic acid while producing 2-sec.-isoamylbenzoylbenzoic acid only to a small extent or, ideally, not at all.

We have found that this object is achieved with a process for preparing an alkyl-substituted aromatic ketone by reacting an alkylbenzene with a carboxylic anhydride in the presence of a Friedel-Crafts catalyst, which comprises performing the reaction in the presence of an effective amount of a tertiary amine or diamine.

If phthalic anhydride is used as the acylating agent and aluminum chloride as the Friedel-Crafts catalyst, the process can be described in terms of the following reaction equation:

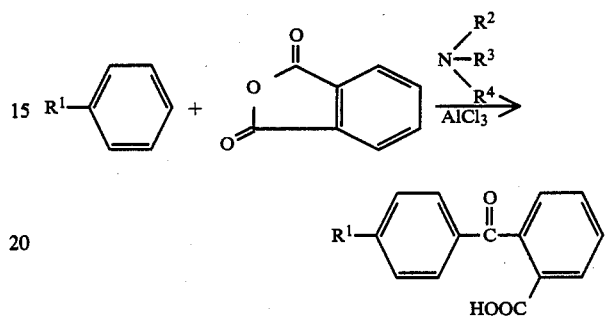

where $R^1$ is alkyl and $R^2$, $R^3$ and $R^4$ are each an aliphatic, cycloaliphatic, araliphatic or aromatic radical.

The tertiary amine added to the reaction mixture combines in situ with the hydrogen halide formed in the course of the reaction to form the ammonium salt. Depending on the amount of tertiary amine, the detachment and isomerization of the alkyl group $R^1$ can be suppressed or prevented. The amine can be substituted by aliphatic, cycloaliphatic, araliphatic and/or aromatic radicals, of which a pair may be linked together to form a cyclic system, which may even be aromatic, or all three may combine to form a bicyclic system. Furthermore, an appropriately substituted diamine may be used in place of the monoamine.

Aliphatic radicals are for example alkyl or alkenyl radicals, in particular of 1 to 20, preferably 1 to 8, carbon atoms, eg. methyl, ethyl, propyl, isopropyl, n-butyl, isobutyl, tert.-butyl, pentyl, isopentyl, hexyl, isooctyl, nonyl or dodecyl on the one hand and isobutenyl, n-pentenyl, n-hexenyl or octenyl on the other. Cycloaliphatic radicals are cycloalkyl or cycloalkenyl radicals of 3 to 8, in particular 5 or 6, ring members, which may contain a further hetero atom such as nitrogen or oxygen, eg. cyclopropyl, cyclobutyl, cyclopentyl, cyclopentenyl, cyclohexyl, cyclohexenyl, cyclooctyl or furfuryl. Araliphatic radicals are for example aralkyl radicals or alkylaryl radicals of 7 to 12 carbon atoms, eg. benzyl or phenylethyl. Aromatic radicals are for example phenyl, naphthyl and 4-pyridyl.

Two of the radicals $R^2$ or $R^4$ can also be linked with each other to form a cyclic system, for example a pyrrolidine, piperidine, piperazine, pyridine, quinoline, quinoxaline, acridine or pyrrole system.

Furthermore, all 3 radicals can combine together to form a bicyclic system, for example a 1-aza- or 1,4-diazabicyclo[2.2.2]octane or 1-azabicyclo[2.2.1]heptane.

The radicals mentioned may additionally bear substituents which are inert under the reaction conditions, such as $C_1$–$C_4$-alkyl groups.

Specific examples of tertiary amines are: trimethylamine, triethylamine, tri-n-propylamine, triisopropylamine, tri-n-butylamine, triisobutylamine, triamylamine, trihexylamine, dimethylethylamine, diisopropylethylamine, diethylisopropylamine, dimethyl-tert.-butylamine, dimethyldodecylamine, N,N-dimethylcyclohexylamine, dicyclohexylethylamine, N,N-dimethylbenzylamine, N,N-diethyl-α-naphthylamine, N-methyl-N-phenyl-1-naphthylamine, trifurfurylamine, N,N-diethylaniline, N-methylpyrrolidine, N-ethylpiperidine, N-propylpiperidine, pyridine, α,β- or 8-picoline, 2,4- or 2,6-lutidine, N-ethylpyrrole, N-methylimidazole, quinoline, isoquinoline, acridine, p-dimethylaminopyridine, N-(4-pyridyl)-pyridine, N,N'-diethylpiperazine, N,N,N',N'-tetraethyl-1,3-propanediamine and 1,4-diazabicyclo[2.2.2]-octane.

It is particularly advantageous to use tertiary alkyl- and/or cycloalkyl-substituted amines and also cyclic or bicyclic amines.

The Friedel-Crafts catalyst used can be one of the customary compounds, eg. iron(III) chloride, boron trifluoride, titanium tetrachloride, aluminum(III) bromide or aluminum(III) chloride, said aluminum halides being preferred.

The amount of tertiary amine ranges in general from 0.1 to about 1.5, preferably from 0.1 to 1, mole per equivalent of carboxylic anhydride. The amount of aluminum halide ranges advantageously from about 2 to 3.5 moles, in particular from 2.1 to 2.5 moles, per equivalent of anhydride.

The activity of the Friedel-Crafts catalyst is modified to a varying extent by the amine used, which is why the amount of aluminum halide used strongly depends on the nature of the amine, sterically hindered aliphatic amines such as triethylamine, diisopropylethylamine and dicyclohexylethylamine or bicyclic amines such as 1,4-diazabicyclo[2.2.2]octane being particularly advantageous. The optimal amount of catalyst in a particular case can be easily determined in preliminary experiments.

The acid anhydride used can be an anhydride of an aliphatic, cycloaliphatic, araliphatic, aromatic or heterocyclic mono- or preferably dicarboxylic acid. Anhydrides of monocarboxylic acids are for example acetic anhydride, propionic anhydride, n-butyric anhydride and benzoic anhydride. Anhydrides of dicarboxylic acids are for example maleic anhydride, succinic anhydride, methylmaleic anhydride, tetraethylsuccinic anhydride and phthalic anhydride.

The reaction can be carried out in the absence or advantageously in the presence of a solvent, suitable solvents being the conventional solvents for Friedel-Crafts reactions, for example chlorobenzene, dichlorobenzene, 1,2-dichloroethane, trichloroethylene, 1,2-dichloropropane, carbon disulfide, nitromethane and nitrobenzene. The amount of solvent is not critical; in general, from 200 to 1000 g per mole of alkylbenzene can be used.

The reaction can be carried out in a conventional manner by reacting the starting materials at from −20° to 100° C., preferably from 0° to 60° C., in particular from 10° to 40° C., under superatmospheric or reduced pressure, preferably under atmospheric pressure.

Advantageously, the acid anhydride is introduced initially together with the solvent, the Friedel-Crafts catalyst is added a little at a time, and the alkylaromatic is added dropwise as a mixture with the amine. In general, stoichiometric amounts of acid anhydride and alkylaromatics are used, although it is also possible to use one of the two starting materials in excess or for example for the alkylaromatic to double up as solvent.

After the reaction has ended, the products are worked up and isolated in a conventional manner, for example by decomposing the resulting catalyst complexes with water and isolating the desired ketone by extraction or crystallization.

Using the process according to the invention, it is surprisingly possible to acylate alkyl-substituted, in particular tert.-alkyl-substituted benzene, by the Friedel-Crafts method without much isomerization of the alkyl radical, which is of interest in particular for the synthesis of tert.-amylbenzoylbenzoic acid. Control of the amount of tertiary amine provides specific control of the ratio of tertiary alkyl to secondary alkyl. The aromatic ketones preparable by the process described are useful intermediates, for example for dyes, auxiliaries, crop protection agents and drugs.

Tert.-amylbenzoylbenzoic acid is an important intermediate for preparing tert.-amylanthraquinone, which is required for the production of hydrogen peroxide.

EXAMPLES 1 TO 3

Preparation of 4-tert.-amyl- and 4-sec.-isoamyl-benzoylbenzoic acid 55 g (0.37 mol) of phthalic anhydride were introduced initially together with aluminum chloride into 260 g of o-dichlorobenzene, and a solution of 55 g (0.37 mol) of tert.-amylbenzene and the tertiary amine listed in the table below was added dropwise in the course of 5 hours, during which the reaction temperature was maintained in the range from 17° to 20° C. Subsequently the mixture was stirred at 40° C. for 1 hour.

As workup, the reaction mixture was poured into dilute sulfuric acid, and the organic phase was extracted with dilute sodium hydroxide solution. The amylbenzoylbenzoic acid was precipitated from the aqueous phase by means of sulfuric acid and then filtered off and dried. The yield and composition of the isomeric mixtures obtained are shown in Table 1.

TABLE 1

| | Reaction of tert.-amylbenzene with phthalic anhydride in the presence of AlCl₃ and tertiary amine. | | | | | | | |
|---|---|---|---|---|---|---|---|---|
| Example | Amine | Amount g | Amine mol | Amount g | AlCl₃ mol | Yield g | Yield % | Isomer ratio tert/sec |
| 1 | 1,4-Diazabicyclo-[2.2.2]octane | 21.9 | 0.19 | 105 | 0.78 | 82 | 75 | 86/14 |
| 2 | Diisopropylethylamine | 26 | 0.2 | 105 | 0.78 | 93 | 85 | 70/30 |
| 3 | Triethylamine | 40 | 0.4 | 158 | 1.18 | 71 | 65 | 99.5/0.5 |

We claim:

1. A process for preparing tertiary amylbenzoylbenzoic acid which comprises:
   reacting amylbenzene with phthalic anhydride in the presence of a Friedel-Crafts catalyst and also in the presence of tertiary amine which is added to the reaction in an amount sufficient to suppress or prevent the detachment or isomerization of the amyl substituent.

2. A process as claimed in claim 1, wherein a tertiary alkyl- or cycloalkyl-substituted amine is used.

3. A process as claimed in claim 1, wherein a cyclic or bicyclic amine is used.

4. A process as claimed in claim 1, wherein from 0.1 to 1.5 moles of tertiary amine are used per equivalent of the phthalic anhydride.

5. A process as claimed in claim 1, wherein the Friedel-Crafts catalyst used is an aluminum halide.

6. A process as claimed in claim 1, wherein the Friedel-Crafts catalyst is a compound selected from the group consisting of iron (III) chloride, boron trifluoride, titanium tetrachloride, aluminum (III) bromide and aluminum (III) chloride.

7. A process as claimed in claim 1, wherein the reaction is carried out at a temperature of from −20° to +100° C.

8. A process as claimed in claim 7, wherein the reaction is carried out at a temperature of from 0° to 60° C.

9. A process as claimed in claim 7, wherein the reaction is carried out at a temperature of from 10° to 40° C.

10. A process as claimed in claim 1, wherein the reaction is carried out at atmospheric pressure.

11. A process as claimed in claim 1, wherein the reaction is carried out in the presence of a solvent for the Friedel-Crafts catalyst.

12. A process as claimed in claim 11, wherein said solvent is selected from the group consisting of chlorobenzene, dichlorobenzene, 1,2-dichloroethane, trichloroethylene, 1,2-dichloropropane, carbon disulfide, nitromethane and nitrobenzene.

13. A process as claimed in claim 1 wherein the tertiary amine is selected from the group consisting of trimethylamine, triethylamine, tri-n-propylamine, triisopropylamine, tri-n-butylamine, triisobutylamine, triamylamine, trihexylamine, dimethylethylamine, diisopropylethylamine, diethylisopropylamine, dimethyl-tert.-butylamine, dimethyldodecylamine, N,N-dimethylcyclohexylamine, dicyclohexylethylamine, N,N-dimethylbenzylamine, N,N-diethyl-α-naphthylamine, N-methyl-N-phenyl-1-naphthylamine, trifurfurylamine, N,N-diethylaniline, N-methylpyrrolidine, N-ethylpiperidine, N-propylpiperidine, pyridine, α,β- or γ-picoline, 2,4- or 2,6-lutidine, N-ethylpyrrole, N-methylimidazole, quinoline, isoquinoline, acridine, p-dimethylaminopyridine, N-(4-pyridyl)-pyridine, N,N'-diethylpiperazine, N,N,N',N'-tetraethyl-1,3-propanediamine and 1,4-diazabicyclo[2.2.2]-octane.

14. A process as claimed in claim 1, wherein the tertiary amine is selected from the group consisting of triethylamine, diisopropylethylamine, dicyclohexylethylamine and 1,4-diazabicyclo-[2.2.2]-octane.

15. A process as claimed in claim 1, wherein the amount of tertiary amine being added is from about 0.1 to 1 mole per equivalent of the phthalic anhydride.

* * * * *